(12) United States Patent
Roth et al.

(10) Patent No.: US 8,247,479 B2
(45) Date of Patent: Aug. 21, 2012

(54) SYMMETRIC AZO COMPOUNDS IN FLAME RETARDANT COMPOSITIONS

(75) Inventors: Michael Roth, Lautertal (DE); Rudolf Pfaendner, Rimbach (DE); Carl-Eric Magnus Wilén, Esbo (FI); Melanie Aubert, Littoinen (FI)

(73) Assignee: BASF SE, Ludwigshafen (DE)

( * ) Notice: Subject to any disclaimer, the term of this patent is extended or adjusted under 35 U.S.C. 154(b) by 204 days.

(21) Appl. No.: 12/527,207

(22) PCT Filed: Feb. 13, 2008

(86) PCT No.: PCT/EP2008/051712
§ 371 (c)(1),
(2), (4) Date: Feb. 5, 2010

(87) PCT Pub. No.: WO2008/101845
PCT Pub. Date: Aug. 28, 2008

(65) Prior Publication Data
US 2010/0144935 A1    Jun. 10, 2010

(30) Foreign Application Priority Data

Feb. 21, 2007  (EP) .................... 07102770

(51) Int. Cl.
C08K 5/34       (2006.01)
C08K 5/3435     (2006.01)
C08K 5/05       (2006.01)
C08G 18/80      (2006.01)
C09B 29/00      (2006.01)
C09B 29/42      (2006.01)

(52) U.S. Cl. ............ 524/103; 524/86; 524/99; 524/100; 524/102; 534/753; 534/766

(58) Field of Classification Search .................. 524/103, 524/86, 99, 100, 102; 534/766, 753
See application file for complete search history.

(56) References Cited

U.S. PATENT DOCUMENTS
5,021,480 A * 6/1991 Ravichandran ................. 524/99
2007/0029531 A1  2/2007 Ronan et al.

FOREIGN PATENT DOCUMENTS
WO    99/00450 A1    1/1999
WO    03/054073 A1   7/2003
WO    2005/030852 A2 4/2005

* cited by examiner

*Primary Examiner* — John J Figueroa
*Assistant Examiner* — Atnaf Admasu
(74) *Attorney, Agent, or Firm* — Tyler A. Stevenson

(57) ABSTRACT

The invention, relates to azo-compounds of formula (I), wherein >N—O—R substituted 2,2,6,6-tetraalkyl-piperidyl groups are present. These azo-compounds have excellent flame retardant properties, either if applied alone, or combined with other compounds, having flame retardant properties.

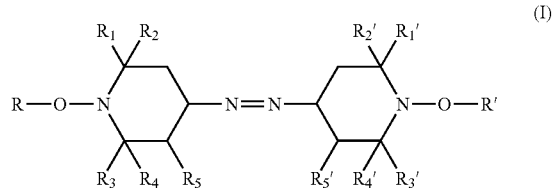

(I)

8 Claims, No Drawings

SYMMETRIC AZO COMPOUNDS IN FLAME RETARDANT COMPOSITIONS

The invention relates to novel azo-compounds, flame retardant compositions comprising the azo-compounds and to the use thereof in polymers, preferably thermoplastic polymers.

Flame retardant(s) (FR, FRs) are added to polymeric materials (synthetic or natural) to enhance the flame retardant properties of the polymers. Depending on their composition, flame retardants may act in the solid, liquid or gas phase, either chemically, e.g. as a spumescent by liberation of nitrogen, and/or physically, e.g. by producing a foam coverage. Flame retardants interfere during a particular stage the combustion process, e.g. during heating, decomposition, ignition or flame spread.

Inorganic and organic compounds with FR-activity have been used for achieving the FR-effect in various types of polymers. Such compounds include halogenated hydrocarbons, phosphorous containing compounds, metal containing compounds, such as metal oxides and hydroxides, and melamine derivatives. Halogenated FRs are very commonly used due to their effectiveness. Nevertheless, the use of halogenated compounds has generally become of an environmental concern.

To diminish the problems relating to halogenated FRs, synergists are often used in combination with halogenated FRs. Synergists are compounds which enhance the flame retarding properties of the halogenated FRs and thus enable the use of halogenated FRs in substantially reduced amounts. Synergistic compounds encompass a group of compounds known as "free radical initiators", which include organic peroxides (see e.g. U.S. Pat. No. 3,058,926), dibenzyl compounds (see e.g. U.S. Pat. No. 3,271,333 and U.S. Pat. No. 3,420,786), disulphides (see e.g. U.S. Pat. No. 3,284,544), hydrazone (see e.g. U.S. Pat. No. 3,269,962), and azo-compounds (see e.g. U.S. Pat. No. 4,237,179, U.S. Pat. No. 3,897,373, U.S. Pat. No. 4,486,347 and FR 1 425 563). Such synergists are used only in combination with other FRs, and typically with said halogenated FRs. The azo-compounds have been used e.g. as azo dyes with an additional function as FR-synergists, and are typically in complex form with transition metal ions, e.g. Cu or Cr.

Non-halogenated N-hydrocarbyloxy hindered amino light stabilizers (NOR-HALS) have also been proposed for solving the problem. These can be used alone, e.g. in place of halogenated FRs, or as synergists for FR-applications (see e.g. WO 99/00450).

According to WO 2005/030852, non-halogenated azo and hydrazine derivatives show themselves flame retarding efficacy when used e.g. in polymeric applications. It is no longer necessary to combine these agents with other FRs, such as conventional organic or inorganic halogenated FR-compounds or with phosphorous, antimony or metal hydroxide FR-compounds.

A disadvantage of the azo-compounds according to WO 2005/030852 is seen in the fact that they degrade when exposed light and, therefore, loose their FR-activity. Therefore, object of the present invention is the preparation of azo-compounds that retain excellent FR-activity, even when exposed to the experimental conditions of artificial weathering.

It has surprisingly been found that azo-compounds, wherein >N—O—R substituted 2,2,6,6-tetraalkypiperidyl groups are present, have excellent FR-properties, either if applied alone, or combined with other compounds having FR-properties. Moreover, flame dripping during the application of fire is significantly reduced.

Subject matter of the present invention are compounds of the formula

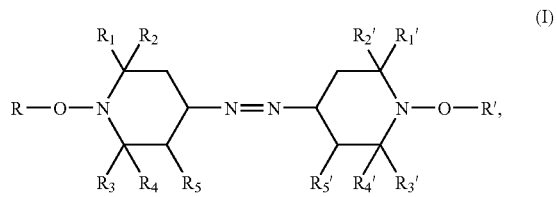

Wherein
R represents $C_1$-$C_{20}$alkyl, hydroxy-$C_2$-$C_8$alkyl, $C_1$-$C_{20}$alkanoyl, $C_7$-$C_{13}$aroyl, $C_2$-$C_{20}$alkenyl, $C_1$-$C_{20}$alkyl or $C_2$-$C_{20}$alkenyl interrupted by at least one heteroatom selected from the group consisting of O, S and N, $C_6$-$C_{20}$aryl, $C_1$-$C_{12}$alkyl-$C_6$-$C_{20}$aryl, $C_6$-$C_{20}$aryl-$C_1$-$C_4$alkyl, mono- or bicyclic $C_5$-$C_{20}$cycloalkyl, mono- or bicyclic $C_1$-$C_{12}$alkyl-$C_5$-$C_{20}$cycloalkyl, or mono- or bicyclic $C_5$-$C_{20}$cycloalkyl-$C_1$-$C_4$alkyl;
$R_1$, $R_2$, $R_3$ and $R_4$ independently of one another represent hydrogen or $C_1$-$C_3$alkyl;
$R_5$ represents hydrogen or methyl; and
$R'$, $R_1'$, $R_2'$, $R_3'$, $R_4'$ and $R_5'$ are as defined as R, $R_1$, $R_2$, $R_3$, $R_4$ and $R_5$.

The compounds (I) are characterized by their excellent flame retardancy. The instant compositions have excellent initial colour and show little yellowing.

The compounds (I) may be used in combination with halogenated and/or non-halogenated FR-compounds, for example non-halogenated FR, to improve flame retarding efficacy. Such halogenated and/or non-halogenated FR-compounds may be conventional organic or inorganic halogenated FR-compounds or phosphorous, antimony or metal hydroxide FR-compounds. The instant compounds may have a synergistic effect on other conventional FR-compounds. In that event, the compounds (I) allow a significant reduction of the amounts needed when applying conventional FR-compounds, such as halogenated or antimony FR-compounds.

The general terms used in the description of the instant invention, unless defined otherwise, are defined as follows:

In a compound (I), the definitions of $R'$, $R_1'$, $R_2'$, $R_3'$, $R_4'$ and $R_5'$ correspond to the definitions of R, $R_1$, $R_2$, $R_3$, $R_4$ and $R_5$.

$C_1$-$C_{20}$alkyl is, e.g. methyl, ethyl or straight chained or branched $C_3$-$C_{30}$alkyl, e.g. n-propyl, isopropyl, n-, iso- or tert-butyl, n-pentyl, isoamyl, neopentyl, 2-ethylbutyl, n-hexyl, 1-methyl-pentyl, 1,3-dimethylbutyl, n-heptyl, isoheptyl, n-octyl, 1,4,4-trimethyl-2-pentyl, 3,4-, 3,5- or 4,5-dimethyl-1-hexyl, 3- or 5-methyl-1-heptyl, 1,1,3,3-tetramethylbutyl, 2-ethylhexyl, branched octyl as obtained from a dimer of isobutylene, n-nonyl, 1,1,3-trimethylhexyl, branched nonyl as obtained from a trimer of tripropylene, 1-methylundecyl, 2-n-butyl-n-octyl, branched dodecyl obtained from a trimer of isobutylene or a tetramer of propylene, branched pentadecyl obtained from a pentamer of propylene, 2-n-hexyl-n-decyl or 2-n-octyl-n-dodecyl.

Hydroxy-$C_2$-$C_8$alkyl is preferably hydroxy-$C_2$-$C_5$alkyl, for example 2-hydroxyethyl, 2- or 3-n-hydroxypropyl or 2-hydroxy-isobutyl (=2-methyl-2-hydroxypropyl).

$C_1$-$C_{20}$alkanoyl is straight chained or branched or unbranched, for example, formyl, acetyl, propionyl, n-butanoyl, isobutanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Preference is given to alkanoyl having 2 to 18, especially 2 to 12, for example 2 to 6 C-atoms. Particular preference is given to acetyl.

$C_7$-$C_{13}$aroyl is, for example, benzoyl or naphthoyl or cinnamoyl.

$C_2$-$C_{20}$alkenyl is, for example, 1-propenyl, allyl, methallyl, 2-butenyl or 2-pentenyl.

$C_6$-$C_{20}$aryl is, for example, phenyl or 1- or 2-napthyl.

$C_1$-$C_{12}$alkyl-$C_6$-$C_{20}$aryl is $C_6$-$C_{20}$aryl, preferably phenyl that is substituted, for example, by from one to three of the $C_1$-$C_4$alkyl radicals described above or by one or two $C_1$-$C_6$alkyl radicals or one $C_1$-$C_{12}$alkyl radical.

$C_6$-$C_{20}$aryl-$C_1$-$C_4$alkyl is preferably phenyl-$C_1$-$C_4$alkyl, e.g. benzyl or 1-phenyl-1-ethyl or 2-phenyl-1-ethyl.

Mono- or bicyclic $C_5$-$C_{20}$cycloalkyl is preferably $C_5$-$C_{12}$cycloalkyl, e.g. cyclopentyl or cyclohexyl.

Mono- or bicyclic $C_1$-$C_{12}$alkyl-$C_5$-$C_{20}$cycloalkyl is preferably $C_5$-$C_{12}$cycloalkyl, e.g. cyclopentyl or cyclohexyl, substituted by, for example, one to three of the $C_1$-$C_4$alkyl radicals, e.g. methyl or tert-butyl, described above or by one or two $C_1$-$C_6$alkyl radicals or one $C_1$-$C_{12}$alkyl radical.

Mono- or bicyclic $C_5$-$C_{20}$cycloalkyl-$C_1$-$C_4$alkyl, is preferably $C_5$-$C_{12}$cycloalkyl-$C_1$-$C_4$alkyl, e.g. cyclopentylmethyl or cyclohexylmethyl.

The compounds according to the invention are obtained by known methods as illustrated below:

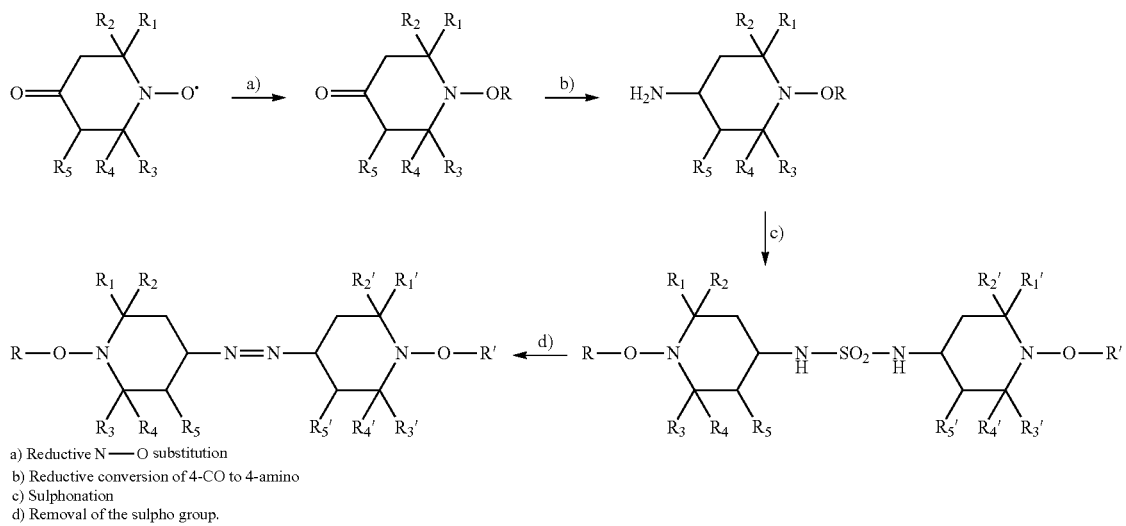

a) Reductive N——O substitution
b) Reductive conversion of 4-CO to 4-amino
c) Sulphonation
d) Removal of the sulpho group.

The process for the preparation of compounds (I) described above starting from the sulphamide or any precursors thereof is also subject matter of the present invention. According to a preferred embodiment, the synthetic route beginning with 4-oxo-TEMPO (=4-oxo-2,2,6,6-tetramethylpiperidine-1-oxide) is illustrated for a representative compound with the following reaction scheme:

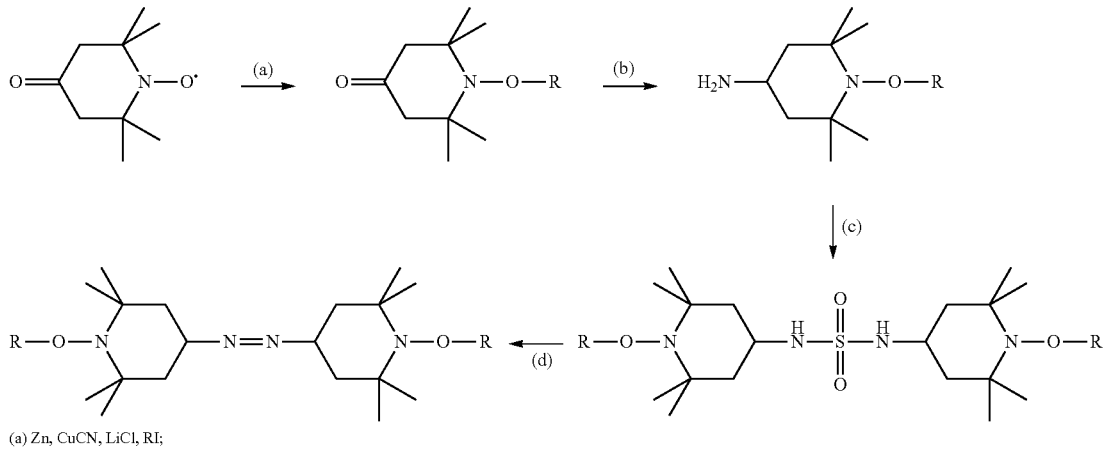

(a) Zn, CuCN, LiCl, RI;
(b) NaBH$_3$CN, CH$_3$CO$_2$NH$_4$;
(c) SO$_2$Cl$_2$;
(d) NaOCH$_3$, t-BuOCl.

According to a preferred embodiment, the invention relates to a compound (I), wherein R represents $C_1$-$C_8$alkyl, hydroxy-$C_2$-$C_8$alkyl, $C_1$-$C_8$alkanoyl, phenyl, $(C_1$-$C_4$alkyl$)_{1-3}$phenyl, phenyl-$C_1$-$C_4$alkyl, $C_5$-$C_6$cycloalkyl, $(C_1$-$C_4$alkyl$)_{1-3}C_5$-$C_6$cycloalkyl, or $(C_1$-$C_4$alkyl$)_{1-3}C_5$-$C_6$cycloalkyl-$C_1$-$C_4$alkyl;

$R_1$, $R_2$, $R_3$ and $R_4$ represent methyl; or

One of $R_1$ and $R_2$ and one of $R_3$ and $R_4$ represents methyl and the other one represents ethyl;

$R_5$ represents hydrogen; and $R'$, $R_1'$, $R_2'$, $R_3'$, $R_4'$ and $R_5'$ are as defined as R, $R_1$, $R_2$, $R_3$, $R_4$ and $R_5$.

According to a particularly preferred embodiment the invention relates to a compound (I), wherein R represents $C_1$-$C_8$alkyl, hydroxy-$C_2$-$C_8$alkyl, $C_1$-$C_8$alkanoyl, phenyl or $C_5$-$C_6$cycloalkyl;

$R_1$, $R_2$, $R_3$ and $R_4$ represent methyl; and $R_5$ represents hydrogen; and $R'$, $R_1'$, $R_2'$, $R_3'$, $R_4'$ and $R_5'$ are as defined as R, $R_1$, $R_2$, $R_3$, $R_4$ and $R_5$.

According to a highly preferred embodiment, the invention relates to a compound (I), wherein R represents $C_1$-$C_4$alkyl, hydroxy-$C_2$-$C_4$alkyl, $C_1$-$C_4$alkanoyl, phenyl or $C_5$-$C_6$cycloalkyl;

$R_1$, $R_2$, $R_3$ and $R_4$ represent methyl; and $R_5$ represents hydrogen; and $R'$, $R_1'$, $R_2'$, $R_3'$, $R_4'$ and $R_5'$ are as defined as R, $R_1$, $R_2$, $R_3$, $R_4$ and $R_5$.

Of particular relevance are compounds (I) selected from the group consisting of

The compounds (I) of the invention are outstandingly suitable for imparting flame-retarding properties to polymers, e.g. synthetic polymers, especially thermoplastics. Therefore, a further embodiment of the invention relates to a composition, which comprises a) A polymer substrate and
b) A compound of the formula (I), Wherein R represents $C_1$-$C_{20}$alkyl, hydroxy-$C_2$-$C_8$alkyl, $C_1$-$C_{20}$alkanoyl, $C_2$-$C_{20}$alkenyl, $C_7$-$C_{13}$aroyl, $C_1$-$C_{20}$alkyl or $C_2$-$C_{20}$alkenyl interrupted by at least one heteroatom selected from the group consisting of O, S and N, $C_2$-$C_{20}$alkinyl, $C_6$-$C_{20}$aryl, $C_1$-$C_{12}$alkyl-$C_6$-$C_{20}$aryl, $C_6$-$C_{20}$aryl-$C_1$-$C_4$alkyl, mono- or bicyclic $C_5$-$C_{20}$cycloalkyl, mono- or bicyclic $C_1$-$C_{12}$alkyl-$C_5$-$C_{20}$cycloalkyl, or mono- or bicyclic $C_5$-$C_{20}$cycloalkyl-$C_1$-$C_4$alkyl;

$R_1$, $R_2$, $R_3$ and $R_4$ independently of one another represent hydrogen or $C_1$-$C_3$alkyl;

$R_5$ represents hydrogen or methyl; and $R'$, $R_1'$, $R_2'$, $R_3'$, $R_4'$ and $R_5'$ are as defined as R, $R_1$, $R_2$, $R_3$, $R_4$ and $R_5$.

The composition according to the invention is obtainable by reactive mixing or compounding methods, particularly reactive extrusion methods, in customary mixing machines, wherein the components a) and b) and, optionally, further additives and polymers are mixed and melted. Suitable machines are known to those skilled in the art. They are predominantly mixers, kneaders and extruders.

The compound (I) of the invention can be added to the polymeric substrate b) alone or as a mixture of one or more compounds (I). The amount is chosen in a manner known so that an industrially acceptable flame retarding property is provided to the polymeric substrate. The amount varies depending on the polymeric substrate used. As an example, amounts from 0.1-20.0 wt-% based on the polymeric substrate b), preferably 0.1-10.0 wt-%, for example 0.1-5.0 wt-%, appear suitable.

The composition according to the invention is characterized by its excellent thermal stability. In the context of the description of the invention, thermal stability is defined as the degree of resistance against foaming upon heating. For a more precise differentiation in thermal stability of flame retardant compositions physico-chemical methods, such as thermogravimetric analysis (TGA) and differential scanning calorimetry (DSC), can be used.

Any type of polymer material can be chosen that is suitable for melt processing at the extruder temperature, preferably at processing temperatures below 300° C. In general the polymer or carrier resin is chosen according to the polymer matrix material that needs flame retardation. Polypropylene and polyethylene are the first choice due to its large availability and easy processing properties. It has been found in this respect that through the use of high density polyethylene, HDPE, colourless flame retardant pellets can be produced, which is advantageous for producing colourless flame retardant polymer compositions. In an alternative embodiment the use of polypropylene has been found advantageous. An acceptable colour of the flame retardant master batches is obtained, combined with high fluidity and excellent flame retardancy and mechanical properties of the composite material.

Other polymers suitable for the polymer composition of the present invention are those polymers, which are processed at temperatures below 300° C. and preferably below 280° C.

A suitable polymer substrate according to Component a) consists of synthetic polymers, such as:

1. Polymers of mono- and di-olefins, for example polypropylene, polyisobutylene, polybutene-1, poly-4-methylpentene-1, polyvinylcyclohexane, polyisoprene or polybutadiene and also polymerisates of cycloolefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

Polyolefins, that is to say polymers of mono-olefins, as mentioned by way of example in the preceding paragraph, especially polyethylene and polypropylene, can be prepared by various processes, especially by the following methods:

a) By free radical polymerisation (usually at high pressure and high temperature);

b) In the presence of a catalyst. The catalyst usually contains one or more metals of Groups IVb, Vb, VIb or VIII of the Periodic Table. Those metals generally have one or more substituents or ligands, such as oxides, halides, alcoholates, esters, ethers, amines, alkyls, alkenyls and/ or aryls, which may be either π- or σ-coordinated. Such metal complexes may be free or fixed to carriers, for example to activated magnesium chloride, titanium(III) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal alkyl oxiranes. This applies particularly to metals of Group(s) Ia, IIa and/or IIIa. The activators may have been modified, for example, with further ester, ether, amine or silyl ether groups. Such catalyst systems are usually referred to as Phillips, Standard Oil Indiana, Ziegler (-Natta), TNZ (DuPont), metallocene or Single Site Catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers, for example ethylene/norbornene (COC), ethylene/1-olefin copolymers wherein the 1-olefin is prepared in situ, propylene/butadiene copolymers, isobutylene/isoprene copolymers, ethylene/vinyl cyclohexene copolymers, ethylene/alkyl acrylate copolymers, ethylene/alkyl methacrylate copolymers, ethylene/vinyl acetate copolymers, ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Polystyrene, poly(p-methylstyrene), poly(α-methylstyrene).

5. Aromatic homopolymers and copolymers derived from vinyl-aromatic monomers, for example styrene, α-methylstyrene, all isomers of vinyltoluene, for example p-vinyltoluene, all isomers of ethylstyrene, propylstyrene, vinylbiphenyl, vinylnaphthalene, vinylanthracene and mixtures thereof; homopolymers and copolymers can have a syndiotactic, isotactic, hemi-isotactic or atactic stereo structure; preference is given to atactic polymers. Also included are stereo block polymers.

6. Homopolymers and copolymers can have a syndiotactic, isotactic, hemi-isotactic or atactic stereo structure; preference is given to atactic polymers. Also included are stereo block polymers.
   a) Copolymers including the already mentioned vinyl-aromatic monomers and comonomers selected from ethylene, propylene, dienes, nitriles, acids, maleic anhydrides, maleic acid amides, vinyl acetate, vinyl chloride and acrylic acid derivatives and mixtures thereof, for example styrene/butadiene, styrene/acrylo-nitrile, styrene/ethylene (interpolymers), styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.
   b) Hydrogenated aromatic polymers prepared by hydrogenation of the polymers mentioned under 6.), especially polycyclohexylethylene (PCHE), often also referred to as polyvinylcyclohexane (PVCH), which is prepared by hydrogenation of atactic polystyrene.
   c) Hydrogenated aromatic polymers prepared by hydrogenation of the polymers mentioned under 6a.).

7. Graft copolymers of vinyl-aromatic monomers, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned above under Paragraph 6, such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulphonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from α,β-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under Paragraph 9 with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Paragraph 1.
12. Homo- and co-polymers of cyclic ethers, such as polyalkylene glycols, polyethylene oxide, polypropylene oxide or copolymers thereof with bisglycidyl ethers.
13. Polyacetals, such as polyoxymethylene, and also those polyoxymethylenes which contain comonomers, for example ethylene oxide; polyacetals modified with thermoplastic polyurethanes, acrylates or MBS.
14. Polyphenylene oxides and sulphides and mixtures thereof with styrene polymers or polyamides.
15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamide 6/I (polyhexamethylene isophthalimide, MXD (m-xylylenediamine); polyamides prepared from hexamethylenediamine and iso- and/or terephthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

Examples of polyamides and copolyamides that can be used are derived from, inter alia, ε-caprolactam, adipic acid, sebacic acid, dodecanoic acid, isophthalic acid, terephthalic acid, hexamethylenediamine, tetramethylenediamine, 2-methyl-pentamethylenediamine, 2,2,4-trimethylhexamethylenediamine, 2,4,4-trimethylhexamethylenediamine, m-xylylenediamine or bis(3-methyl-4-aminocyclohexyl)methane; and also semiaromatic polyamides such as polyamide 66/6I, for example consisting of 70-95% polyamide 6/6 and 5-30% polyamide 6/I; and also tricopolymers in which some of the polyamide 6/6 has been replaced, for example consisting of 60-89% polyamide 6/6, 5-30% polyamide 6/I and 1-10% of another aliphatic polyamide; the latter may consist of, for example, polyamide 6, polyamide 11, polyamide 12 or polyamide 6/12 units. Such tricopolymers may accordingly be designated polyamide 66/6I/6, polyamide 66/6I/11, polyamide 66/6I/12, polyamide 66/6I/610 or polyamide 66/6I/612.

16. Polyureas, polyimides, polyamide imides, polyether imides, polyester imides, polyhydantoins and polybenzimidazoles.
17. Polyesters derived from dicarboxylic acids and dialcohols and/or from hydroxycarboxylic acids or the corresponding lactones, such as polyethylene terephthalate, polypropylene terephthalate, polybutylene terephthalate, poly-1,4-dimethylolcyclohexane terephthalate, polyalkylene naphthalate (PAN) and polyhydroxy-benzoates, and also block polyether esters derived from polyethers with hydroxyl terminal groups; and also polyesters modified with polycarbonates or MBS.
18. Polycarbonates and polyester carbonates.
19. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preference is given to compositions wherein the thermoplastic polymer is high-impact polystyrene (HIPS), expandable polystyrene (EPS), expanded polystyrene (XPS), polyphenylene ether (PPE), polyamide, polyester, polycarbonate (PC) or a polymer blend of the type ABS (acrylonitrile-butadiene-styrene) or PC/ABS (polycarbonate/acrylonitrile-butadiene-styrene) or PPE/HIPS (polyphenylene ether/high-impact polystyrene), especially a polyamide, polyester or a PPE/HIPS blend.

Special preference is given to polymer compositions according to the invention that comprise a filler or a reinforcing agent, especially glass-fibre-reinforced polymers, e.g. glass-fibre-reinforced polyamide.

A preferred embodiment relates to flame retardant compositions, wherein the polymer substrate a) consists of polyethylene, polypropylene or blends of polypropylene with polyolefins. Examples are blends of polypropylene with polyethylene selected from the group consisting of high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) and ethylene-propylene-diene terpolymers (EPDM) containing small proportions of diene.

The instant invention further pertains to a flame retardant composition, which comprises, in addition to the components a) and b), as defined above, c) further additives selected from the group consisting of polymer stabilizers and additional flame-retardants, such as melamine containing flame retardants, phosphorus containing flame-retardants, further nitrogen containing flame-retardants other than melamine containing flame retardants, halogenated flame-retardants and inorganic flame-retardants.

Stabilizers are preferably halogen-free and selected from nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

Additional flame-retardants as of present component c) are known components, items of commerce or can be obtained by known methods.

Representative melamine containing flame retardants, in addition to the azo-compounds (I) defined above with regard to component a), are for example, melamine comprising compounds, wherein the melamine structure: 1,3,5-triazine-2,4,6-triamin (=cyanuric acid triamide) or condensates thereof are present. The definition applies to monomeric, oligomeric or polymeric compounds of melamine, condensates of melamine or condensates with of melamine and phosphoric thereof.

Preferred melamine comprising compounds are melamine cyanurate, melamine phosphate, dimelamine phosphate, melamine pyrophosphate, melamine polyphosphate, melamine borate, melamine ammonium phosphate, melamine ammonium polyphosphate, melamine ammonium pyrophosphate, melem, melam or melon or polyphosphates of melem, melam or melon.

Representative phosphorus containing flame-retardants, in addition to the melamine compounds defined above with regard to component b), are for example:

Tetraphenyl resorcinol diphosphite (FYROLFLEX® RDP, Akzo Nobel), tetrakis(hydroxymethyl)phosphonium sulphide, triphenyl phosphate, diethyl-N,N-bis(2-hydroxyethyl)-aminomethyl phosphonate, hydroxyalkyl esters of phosphorus acids, ammonium polyphosphate (APP) or (HOSTAFLAM® AP750), resorcinol diphosphate oligomer (RDP), phosphazene flame-retardants and ethylenediamine diphosphate (EDAP).

Further nitrogen containing flame-retardants other than melamine containing flame retardants, are, for example, isocyanurate flame-retardants, such as polyisocyanurate, esters of isocyanuric acid or isocyanurates. Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate.

Further examples are: benzoguanamine, tris(hydroxyethyl)isocyanurate, allantoin, glycouril, melamine cyanurate, urea cyanurate or ammonium polyphosphate.

Representative organohalogen flame-retardants are, for example:

Polybrominated diphenyl oxide (DE-60F, Great Lakes Corp.), decabromodiphenyl oxide (DBDPO; SAYTEX® 102E), tris[3-bromo-2,2-bis(bromomethyl)propyl]phosphate (PB 370®, FMC Corp.), tris(2,3-dibromopropyl)phosphate, tris(2,3-dichloropropyl)phosphate, chlorendic acid, tetrachlorophthalic acid, tetrabromophthalic acid, poly-β-chloroethyl triphosphonate mixture, tetrabromobisphenol A bis(2,3-dibromopropyl ether) (PE68), brominated epoxy resin, ethylene-bis(tetrabromophthalimide) (SAYTEX® BT-93), bis(hexachlorocyclopentadieno)-cyclooctane (DECLORANE PLUS®), chlorinated paraffins, octabromodiphenyl ether, hexachlorocyclopentadiene derivatives, 1,2-bis(tribromophenoxy)ethane (FF680), tetrabromobisphenol A (SAYTEX® RB100), ethylene bis-(dibromo-norbornanedicarboximide) (SAYTEX® BN-451), bis-(hexachlorocycloentadeno)cyclooctane, PTFE, tris-(2,3-dibromopropyl)-iso-cyanurate, and ethylene-bis-tetrabromophthalimide.

The flame-retardant mentioned above routinely combined with inorganic (hydr)oxide synergists. Most common for this use are aluminum (hydr)oxide, such as $Al(OH)_3$ or AlOOH, magnesium hydroxide, zinc or antimony oxides, e.g. $Sb_2O_3$ or $Sb_2O_5$. Boron compounds are suitable, too.

The above-mentioned additional flame-retardant compounds are advantageously contained in the composition of the invention in an amount from about 0.25% to about 45.0% by weight of the organic polymer substrate; for instance about 0.25% to about 35.0%; for example about 0.25% to about 30.0% by weight of the polymer.

As mentioned above, the composition according to the invention may additionally contain one or more conventional additives, for example selected from pigments, dyes, plasticizers, antioxidants, thixotropic agents, levelling assistants, basic co-stabilizers, metal passivators, metal oxides, organophosphorus compounds, further light stabilizers and mixtures thereof, especially pigments, phenolic antioxidants, calcium stearate, zinc stearate, UV absorbers of the 2-hydroxy-benzophenone, 2-(2'-hydroxyphenyl)benzotriazole and/or 2-(2-hydroxyphenyl)-1,3,5-triazine groups.

The additives mentioned above are preferably contained in an amount of 0.01 to 10.0%, especially 0.05 to 5.0%, relative to the weight of the polymer substrate b).

The present invention accordingly relates also to the use of the compounds (I) according to the invention for imparting flame-resistant properties to a polymer substrate, for example synthetic polymers, especially to thermoplastics, and also to a method of imparting flame-resistant properties to synthetic polymers, wherein at least one compound (I) according to the invention is incorporated in the polymer substrate or is applied to their surface.

The incorporation of the compounds (I) and the optional additional components, as defined above, into the polymer substrate is carried out by known methods such as dry blending in the form of a powder, or wet mixing in the form of solutions, dispersions or suspensions for example in an inert solvent, water or oil. The compound (I) and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc.), e.g. as a dry mixture or powder, or as a solution or dispersion or suspension or melt.

The addition of the additional components to the polymer substrate b) can be carried out in all customary mixing machines in which the polymer is melted and mixed with the additives. Suitable machines are known to those skilled in the art. They are predominantly mixers, kneaders and extruders.

Particularly preferred processing machines are twin-screw extruders e.g. contra-rotating or co-rotating twin-screw extruders. Other processing machines are planetary-gear extruders, ring extruders or co-kneaders. It is also possible to use processing machines provided with at least one gas or vapour removal compartment to which a vacuum can be applied.

Suitable extruders and kneaders are described, for example, in *Handbuch der Kunststoffextrusion*, Editors F. Hensen, W. Knappe, H. Potente, *Vol. 1 Grundlagen,* 1989, pp. 3-7, ISBN:3-446-14339-4 and *Vol. 2 Extrusionsanlagen* 1986, ISBN 3-446-14329-7.

For example, the screw length is 1-60 screw diameters, preferably 35-48 screw diameters. The rotational speed of the screw is preferably 10-600 rotations per minute (rpm), very particularly preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

In such operations, the polymer can be used in the form of powder, granules, solutions, and suspensions or in the form of lattices.

The azo-compound (I) a) and optional further additives can also be added to the polymer substrate b) in the form of a master batch ("concentrate") which contains the components in a concentration of, for example, about 1.0% to about 40.0% and preferably 2.0% to about 20.0% by weight incorporated in a polymer. In such operations, the polymer can be used in the form of powder, granules, solutions, and suspensions or in the form of lattices.

Incorporation can take place prior to or during the shaping operation. The materials containing the additives of the invention described herein preferably are used for the production of molded articles, for example roto-molded articles, injection molded articles, profiles and the like, and especially a fiber, spun melt non-woven, film or foam.

Thus, present invention further pertains to molded or extruded articles, such as pipes, wire and cables, fibers, spun melt non-woven or a foam comprising the composition of the invention.

The following Examples illustrate the invention.

A) SYNTHETIC EXAMPLES

Example 1

1. Preparation of bis-(1-cyclohexyloxy-2,2,6,6-tetramethylpiperidyl)-4-diazene

1.1 Preparation of N-cyclohexyloxy-4-oxo-2,2,6,6-tetramethylpiperidine

A suspension of zinc powder (15.6 mmol, 1.02 g) and a catalytic amount of 1,2-dibromoethane (50 µl) in 2 ml of THF is refluxed for 1 min under argon atmosphere. Upon cooling the suspension to ambient temperature, trimethylchlorosilane (62 µl) is added, and the reaction mixture stirred for 15 min. A solution of iodocyclohexane (15.0 mmol, 1.94 ml), diluted in 5 ml of THF, is added drop-wise to the suspension, and the reaction mixture is stirred at 30° C. for 12 h. 3.5 ml (~5 mmol) of the solution thus obtained is transferred to a solution of CuCN (5.0 mmol, 0.45 g) and oven-dried LiCl (10.5 mmol, 0.45 g) in 5 ml of THF, previously cooled to −10° C. Upon stirring for 10 min at 0° C., the reaction mixture is cooled to −20° C. and (15.5 mmol, 2.60 g) 4-oxo-TEMPO (=4-oxo-2,2,6,6-tetramethylpiperidine-1-oxide) in 5 ml of THF is added drop-wise for 5 min. After stirring for 20 min, the initial reddish color of the solution disappears. The solution is warmed up to ambient temperature and concentrated under reduced pressure. The residue is diluted in ether (100 ml), and the ether solution is washed with water (100 ml), dried over $Na_2SO_4$ and concentrated under reduced pressure. The residue is subjected to flash-chromatography (light petroleum ether/ethylacetate 40/1) to yield the NOR-compound as a colorless oil (0.89 g, 70%). $^1$H-NMR (CDCl$_3$): δ=3.66 (m, 1H, CH—O), 2.54 (d, J=12.9 Hz, 2H, CH—O), 2.21 (d, J=12.7 Hz, 2H, CH—O), 2.08 (m, 2H), 1.75 (m, 2H), 1.57 (m, 1H), 1.26 (s, 5H, CH$_3$), 1.22-1.18 (m, 6H), 1.14 (s, 6H, CH$_3$); $^{13}$C-NMR (CDCl$_3$): δ=208.7, 82.2, 62.8, 33.8, 32.6, 25.8, 25.0, 22.8, 22.6.

1.2 Preparation of 4-amino-N-cyclohexyloxy-2,2,6,6-tetramethylpiperidine

Ammonium acetate (592.0 mmol, 45.63 g), followed by the addition of molecular sieves (10$^{-10}$ m, 8 g), and 95% NaBH$_3$CN (59.2 mmol, 3.92 g), are added under argon atmosphere at ambient temperature to a solution of N-cyclohexyloxy-4-oxo-2,2,6,6-tetramethylpiperidine (59.2 mmol, 15.0 g) in 300 ml dry methanol. After stirring for 12 h, CH$_2$Cl$_2$ is added (1000 ml). The solution is washed with 1N NaOH (2×1000 ml), dried over Na$_2$SO$_4$ and concentrated under reduced pressure. The residue is subjected to flash-chromatography (CH$_2$Cl$_2$/methanol 9:1) to yield the NOR compound as a colorless oil (9.94 g, 66%) that solidifies upon storage at 4° C. $^1$H-NMR (CDCl$_3$): δ=3.57 (m, 1H, CH—O), 3.01 (m, 1H, CH—NH$_2$), 2.03 (m, 2H), 1.73-1.64 (m, 4H), 1.54 (m, 4H), 1.34-1.2 (m, 6H), 1.16 (s, 6H, CH$_3$), 1.12 (s, 6H, CH$_3$); $^{13}$C-NMR (CDCl$_3$): δ=81.8, 59.8, 50.4, 42.1, 34.4, 32.8, 25.9, 25.0, 21.1.

1.3 Preparation of bis-(1-cyclohexyloxy-2,2,6,6-tetramethylpiperidyl)-4-sulphamide Under nitrogen atmosphere, a solution of sulphuryl chloride (2.7 mmol, 0.25 ml) in 10 ml of dichloromethane is added drop-wise at 0° C. to a solution of 4-amino-N-cyclohexyloxy-2,2,6,6-tetramethylpiperidine (6.70 mmol, 1.70 g) and triethylamine (13.4 mmol, 1.84 ml) in 20 ml of dichloromethane. Upon completion of the addition, the reaction mixture is stirred for 4 hours at 0° C. The reaction is diluted with water (50 ml) and dichloromethane. The organic phase is washed with water (3×50 ml). After drying the organic phase (Na$_2$SO$_4$) the solvent is evaporated under reduced pressure. The residue is washed with diethyl ether to give bis-(1-cyclohexyloxy-2,2,6,6-tetramethyl-piperidyl)-4-sulphamide as a white powder (1.03 g, 67%). $^1$H-NMR (CDCl$_3$): δ=3.87 (d, J=8.3 Hz, 2H, NH), 3.50 (m, 4H, CH—NH and CH—O), 2.02 (m, 4H), 1.88 (m, 2H), 1.84 (m, 2H), 1.75 (m, 4H), 1.57 (m, 4H), 1.40 (t, J=11.9 Hz, 4H), 1.29-1.20 (m, 8H), 1.17 (s, 12H, CH$_3$), 1.16 (s, 12H, CH$_3$); $^{13}$C-NMR (CDCl$_3$): δ=82.0, 59.9, 47.2, 45.9, 34.3, 32.8, 25.9, 25.0, 20.9.

1.4 Preparation of bis-(1-cyclohexyloxy-2,2,6,6-tetramethylpiperidyl)-4-diazene A solution of sodium methoxide (3.6 mmol, 0.19 g) in 4 ml of dry methanol is added drop wise at 0° C. to a solution of bis-(1-cyclohexyloxy-2,2,6,6-tetramethylpiperidyl)-4-sulphamide (0.90 mmol, 0.51 g) in 20 ml of dry methanol. After stirring for 30 min, a solution of tert-butyl hypochlorite (1.70 mmol, 0.16 g) in 5 ml of dry methanol is added, and the mixture is stirred at 0° C. for 1 h. Water is added to the suspension and extracted with CH$_2$Cl$_2$ (2×30 ml). The organic phase is washed with water (1×30 ml), dried over Na$_2$SO$_4$. The solvent is evaporated to give bis-(1-cyclohexyloxy-2,2,6,6-tetramethylpiperidyl)-4-diazene (0.43 g, 94%) as a white powder (m.p. 127° C.). $^1$H-NMR (CDCl$_3$): δ=3.65 (m, 4H, CH—N and CH—O), 2.05 (m, 4H), 1.9 (t, J=12.6 Hz; 4H, CH$_2$—CCH$_3$), 1.73 8 m, 4H), 1.59-1.51 (m, 6H), 1.31-1.18 (m, 10H), 1.23 (s, 12H, CH$_3$), 1.16 (s, 12H, CH$_3$); $^{13}$C-NMR (CDCl$_3$): δ=81.0, 67.3, 58.3, 42.6, 33.3, 31.8, 24.8, 24.0, 19.9.

Example 2

2. Preparation of bis(1-propoxy-2,2,6,6-tetramethylpiperidyl)-4-diazene

2.1 Preparation of N-propoxy-4-oxo-2,2,6,6-tetramethylpiperidine

N-Propoxy-4-oxo-2,2,6,6-tetramethylpiperidine (3.2 g, 26%) is synthesized in the same manner as described above with regard to N-cyclohexyloxy-4-oxo-2,2,6,6-tetramethylpiperidine, with the exception of the addition of Zn (61.1 mmol, 4.00 g), 1,2-dibromoethane (200 µl), trimethyl-chlorosilane (250 µl), iodopropane (58.8 mmol, 10.0 g), CuCN (53.6 mmol, 4.80 g), LiCl (114 mmol, 4.80 g) and 4-oxo- TEMPO (58.8 mmol, 10.0 g). $^{1}$H-NMR (CDCl$_3$): δ=3.78 (t, J=6.7 Hz, 2H, O—CH$_2$), 2.55 (d, J=12.7 Hz, 2H, CH$_2$—CCH$_3$), 2.20 (d, J=12.7 Hz, 2H, CH$_2$—CCH$_3$), 1.57 (m, 2H, CH$_2$—CH$_3$), 1.28 (s, 6H, C—CH$_3$), 1.14 (s, 6H, C—CH$_3$), 0.95 (t, J=7.45 Hz, 3H, CH$_2$—CH$_3$); $^{13}$C-NMR (CDCl$_3$): δ208.5, 78.5, 63.0, 53.3, 32.5, 22.5, 21.8, 10.9.

2.2 Preparation 4-amino-N-propoxy-2,2,6,6-tetramethylpiperidine

4-Amino-N-propoxy-2,2,6,6-tetramethylpiperidine (1.6 g, 62%) is prepared from N-propoxy-4-oxo-2,2,6,6-tetramethylpiperidine (12.2 mmol, 2.60 g) by the same method as described above, with the exception of the addition of ammonium acetate (122 mmol, 9.40 g), 6 g molecular sieves (10$^{-10}$ m) and 95% NaBH$_3$CN (12.2 mmol, 0.8 g). $^{1}$H-NMR (CDCl$_3$); δ=3.61 (t, J=6.6 Hz, 2H, CH$_2$—O), 2.99 (m, 1H, NH$_2$—CH), 1.58 (d, J=11.4 Hz, 2H, NH$_2$), 1.46 (m, 2H, CH$_2$—CH$_3$), 1.20 (m, 4H), 1.16 (s, 6H, CH$_3$), 1.13 (s, 6H, CH$_3$), 0.93 (t, J=7.4 Hz, 3H, CH$_2$—CH$_3$); $^{13}$C-NMR (CDCl$_3$): δ=78.3, 59.8, 49.9, 41.4, 33.2, 21.9, 20.9, 10.9.

2.3 Preparation of bis-(1-propoxy-2,2,6,6-tetramethylpiperidyl)-4-sulphamide bis-(1-Propoxy-2,2,6,6-tetramethylpiperidyl)-4-sulphamide (1.0 g, 68%) is synthesized from 4-amino-N-propoxy-2,2,6,6-tetramethylpiperidine (7.5 mmol, 1.6 g) in the same manner as described above with regard to bis-(1-cyclohexyloxy-2,2,6,6-tetramethylpiperidyl)-4-sulphamide, with the exception of the addition of sulphuryl chloride (2.8 mmol, 0.25 ml) and triethylamine (15.0 mmol, 2.0 ml). $^{1}$H-NMR (CDCl$_3$): δ=3.94 (d, J=8.2 Hz, 2H, NH), 3.69 (t, J=6.6 Hz, 4H, CH$_2$—O), 3.50 (m, 2H, NH—CH), 1.86 (d, J=12.0 Hz, 4H), 1.56 (m, 4H), 1.41 (t, J=12.4 Hz, 4H), 1.19 (s, 12H, CH$_3$), 1.18 (s, 12H, CH$_3$), 0.95 (t, J=7.4 Hz, 6H, CH$_2$—CH$_3$); $^{13}$C-NMR (CDCl$_3$) δ=78.5, 59.9, 46.7, 45.8, 32.9, 21.9, 20.7, 10.9.

2.4 Preparation of bis-(1-propoxy-2,2,6,6-tetramethylpiperidyl)-4-diazene bis-(1-Propoxy-2,2,6,6-tetramethylpiperidyl)-4-diazene (0.82 g, 95%; m.p. 162° C.) is synthesized in the same manner as described above with regard to bis-(1-cyclohexyloxy-2,2,6,6-tetramethylpiperidyl)-4-diazene, with the exception of the addition of sodium methoxide (8.2 mmol, 0.45 g), bis(1-propoxy-2,2,6,6-tetramethylpiperidyl)-4-sulphamide (2.04 mmol, 1.0 g) and tert-butyl hypochlorite (4.3 mmol, 0.4 g). $^{1}$H-NMR (CDCl$_3$): δ=3.65 (t, J=6.6 Hz, 4H, CH$_2$—O), 3.58 (m, 2H, N—CH), 1.81 (t, J=12.4 Hz, 4H), 1.47 (m, 8H), 1.16 (s, 12H, CH$_3$), 1.09 (s, 12H, CH$_3$), 0.95 (t, J=7.4 Hz, 6H, CH$_2$—CH$_3$); $^{13}$C-NMR (CDCl$_3$): δ=78.5, 68.2, 59.3, 43.1, 33.1, 22.0, 21.0, 10.9.

Example 3

3. Preparation of bis(1-octyloxy-2,2,6,6-tetramethylpiperidyl)-4-diazene

3.1 Preparation of N-octyloxy-4-oxo-2,2,6,6-tetramethylpiperidine

N-octyloxy-4-oxo-2,2,6,6-tetramethylpiperidine (30.3 g, 36%) is synthesized in the same manner as described above with regard to N-cyclohexyloxy-4-oxo-2,2,6,6-tetramethylpiperidine, with the exception of the addition of Zn (294.0 mmol, 19.25 g), 1,2-dibromoethane (900 µl), trimethylchlorosilane (1.2 ml), iodooctane (294 mmol, 70.6 g), CuCN (294 mmol, 26.3 g), LiCl (588 mmol, 25.0 g) and 4-oxo-TEMPO (294 mmol, 50.0 g). $^{1}$H-NMR (CDCl$_3$): δ=3.69 (t, J=6.5 Hz, 2H, O—CH$_2$), 2.55 (d, J=12.8 Hz, 2H, CH$_2$—CCH$_3$), 2.20 (d, J=12.8 Hz, 2H, CH$_2$—CCH$_3$), 1.54 (m, 2H, CH$_2$—CH$_3$), 1.36 (m, 2H, CH$_2$), 1.28 (m, 14H, CH$_2$ and C—CH$_3$), 1.15 (s, 6H, C—CH$_3$), 0.88 (t, J=6.8 Hz, 3H, CH$_2$—CH$_3$); $^{13}$C-NMR (CDCl$_3$) δ=208.4, 77.1, 62.9, 53.3, 32.5, 31.8, 29.6, 29.2, 28.6, 26.4, 22.6, 22.5, 14.1.

3.2 Preparation 4-amino-N-octyloxy-2,2,6,6-tetramethylpiperidine

4-Amino-N-octyloxy-2,2,6,6-tetramethylpiperidine (16.7 g, 62%) is prepared from N-octyloxy-4-oxo-2,2,6,6-tetramethylpiperidine (95.4 mmol, 27.0 g) by the same method as described above, with the exception of the addition of ammonium acetate (954.5 mmol, 73.5 g), 15 g molecular sieves (10$^{-10}$ m) and 95% NaBH$_3$CN (95.4 mmol, 6.32 g). $^{1}$H-NMR (CDCl$_3$); δ=3.61 (t, J=6.6 Hz, 2H, CH$_2$—O), 2.99 (m, 1H, NH$_2$—CH), 1.63 (d, J=11.4 Hz, 2H, NH$_2$), 1.46 (m, 4H, CH$_2$—CH$_3$), 1.26 (m, 12H), 1.15 (s, 6H, CH$_3$), 1.12 (s, 6H, CH$_3$), 0.87 (t, J=7.4 Hz, 3H, CH$_2$—CH$_3$); $^{13}$C-NMR (CDCl$_3$): δ=77.0, 59.8, 50.1, 41.4, 33.2, 31.8, 29.6, 29.2, 28.6, 26.4, 21.3, 21.4, 14.1.

3.3 Preparation of bis-(1-octyloxy-2,2,6,6-tetramethylpiperidyl)-4-sulphamide Bis-(1-octyloxy-2,2,6,6-tetramethylpiperidyl)-4-sulphamide (10.5 g, 60%) is synthesized from 4-amino-N-octyloxy-2,2,6,6-tetramethylpiperidine (70.4 mmol, 20.0 g) in the same manner as described above with regard to bis-(1-cyclohexyloxy-2,2,6,6-tetramethylpiperidyl)-4-sulphamide, with the exception of the addition of sulphuryl chloride (28.2 mmol, 2.26 ml) and triethylamine (141 mmol, 19.5 ml). $^{1}$H-NMR (CDCl$_3$): δ=4.07 (d, J=8.3 Hz, 2H, NH), 3.63 (t, J=6.4 Hz, 4H, CH$_2$—O), 3.40 (m, 2H, NH—CH), 1.77 (d, J=12.0 Hz, 4H), 1.43 (m, 6H), 1.33 (m, 4H), 1.21 (m, 18H, CH$_3$), 1.10 (s, 12H, CH$_3$), 1.09 (s, 12H, CH$_3$), 0.81 (t, J=7.2 Hz, 6H, CH$_2$—CH$_3$); $^{13}$C-NMR (CDCl$_3$) δ=77.0, 59.8, 46.6, 45.7, 32.9, 31.9, 29.7, 29.2, 28.7, 26.4, 22.6, 20.7, 14.1.

3.4 Preparation of bis-(1-octyloxy-2,2,6,6-tetramethylpiperidyl)-4-diazene bis-(1-octyloxy-2,2,6,6-tetramethylpiperidyl)-4-diazene (6.9 g, 78%; m.p. 71° C.) is synthesized in the same manner as described above with regard to bis-(1-cyclohexyloxy-2,2,6,6-tetramethylpiperidyl)-4-diazene, with the exception of the addition of sodium methoxide (63.6 mmol, 3.40 g), bis (1-propoxy-2,2,6,6-tetramethylpiperidyl)-4-sulphamide (15.9 mmol, 10.0 g) and tert-butyl hypochlorite (31.8 mmol, 3.45 g). $^{1}$H-NMR (CDCl$_3$): δ=3.68 (t, J=6.6 Hz, 4H, CH$_2$—O), 3.57 (m, 2H, N—CH), 1.82 (t, J=12.4 Hz, 4H), 1.45 (m, 8H), 1.28 (m, 4H), 1.21 (m, 16H), 1.15 (s, 12H, CH$_3$), 1.08 (s, 12H, CH$_3$), 0.81 (t, J=7.0 Hz, 6H, CH$_2$—CH$_3$); $^{13}$C-NMR (CDCl$_3$): δ=76.0, 67.1, 58.3, 42.0, 32.1, 30.8, 28.7, 28.3, 27.7, 25.4, 21.6, 19.9, 13.1.

B) APPLICATION EXAMPLES

Materials and Methods: Process and Flame Tests

Unless stated otherwise, commercial polypropylene (MOPLEN HF500N, manufacturer: Basell) is extruded in a co-rotating twin-screw extruder ZSK25 from Werner & Pfleiderer at a temperature of $T_{max}$: 230° C. (heating zones 1-6), throughput rate of 4 kg/h and 100 rpm under addition of basic-level stabilization (0.3% IRGANOX B225+0.05% Ca-stearate/IRGANOX B225: 1:1 mixture of IRGAFOS 168 and IRGANOX 1010) and the additives listed in Tables 1 and 2. After cooling in a water bath the polymer strand is granulated.

NOR1: FLAMESTAB NOR116 (commercial product Ciba Specialty Chemicals):

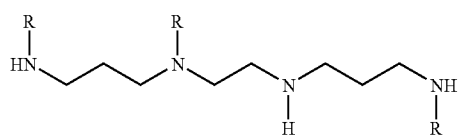

R = 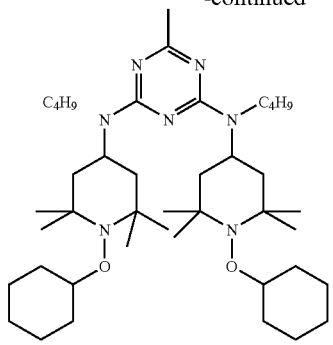

Test specimen are either prepared by compression molding in a hot press (film thickness 200 μm, 250×110 mm, Fontine TP200, $p_{max}$: 50 kN, 230° C.) or by injection molding (100× 100 mm plaques, thickness:1 mm, Arburg 370S, 225° C.).

The test samples are investigated for flame retardancy in accordance to DIN 4102-B2 (edge ignition, flame length=40 mm). Artificial weathering is performed in a Weather-O-meter Ci 65 A from Atlas (BPT=63° C., 60% RH, water spray).

TABLE 1

(flame tests on 200 μm pressed films according to DIN 4102-B2, edge ignition, 40 mm flame): Low values for weight loss and burn length reflect increased flame retardancy.

| Example | Additives | Weight loss [%] | Burn length [mm] | Burning drips | Pass/Fail |
|---|---|---|---|---|---|
| Comparison 1 | w/o | 100 | 190 | yes | Fail |
| Inventive 1 | 0.50% | 2.1 | 93 | no | Pass |
| Inventive 2 | 0.50% | 4.8 | 85 | no | Pass |

TABLE 2

(flame tests on 1 mm injection molded plaques according to DIN 4102-B2 before and after artificial weathering): Low values for weight loss and burn length reflect increased flame retardancy.

| | | Before artificial weathering | | | After 400 h artificial weathering | | |
|---|---|---|---|---|---|---|---|
| Example | Additives | Weight loss [%] | Burn length [mm] | Pass/Fail | Weight loss [%] | Burn length [mm] | Pass/Fail |
| Comparison 1 | w/o | 100 | 100 | Fail | 100 | 100 | Fail |

TABLE 2-continued

| Example | Additives | | | | | | |
|---|---|---|---|---|---|---|---|
| Comparison 2 | 0.50% 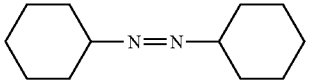 | 12.9 | 47 | Pass | 39 | 93 | Fail |
| Comparison 3 | 0.25% 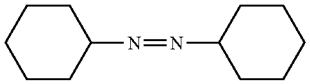 + 0.25% NOR1 | 14.5 | 44 | Pass | 21.1 | 75 | Fail |
| Comparison 4 | 0.5% NOR1 | 49.4 | 80 | Fail | 42.9 | 100 | Fail |
| Inventive 1 | 0.50% 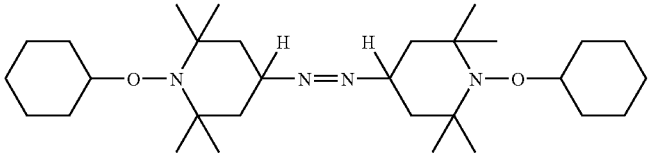 | 8.9 | 37 | Pass | 13 | 44 | Pass |
| Inventive 2 | 0.50% 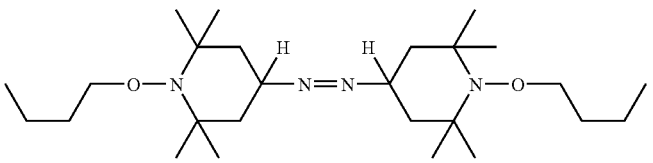 | 5.2 | 27 | Pass | 5.4 | 27 | Pass |

(flame tests on 1mm injection molded plaques according to DIN 4102-B2 before and after artificial weathering, 20 mm flame, PDR100077): Low values for weight loss and burn length reflect increased flame retardancy.

| Example | Additives | After 2000 h artificial weathering | | |
|---|---|---|---|---|
| | | Weight loss/[%] | Burn length/[mm] | Pass/Fail |
| Comparison 1 | w/o | plaques | destroyed | after 400 h |
| Comparison 2 | 0.5% 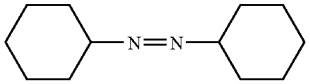 | plaques | destroyed | after 800 h |
| Comparison 3 | 0.25% 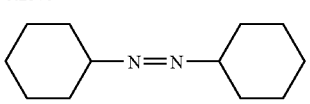 + 0.25% NOR1 | plaques | destroyed | after 1200 h |
| Comparison 4 | 0.5% NOR1 | test | failed | After 800 h |
| Inventive 1 | 0.5% 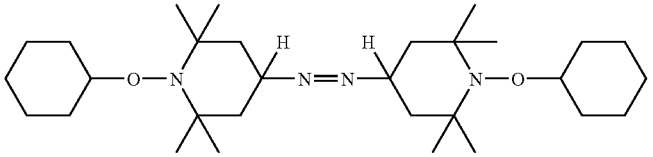 | 11.3 | 43 | Pass |

TABLE 2-continued

| | | | 7 | 30 | Pass |

Inventive 2  0.5%

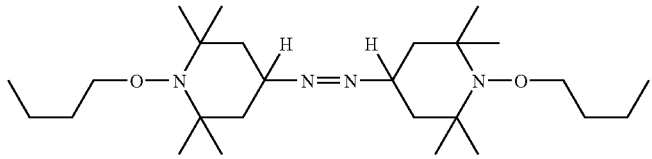

The azo-compound without additional light stabilizing effect has lost FR-activity after a short exposure to light whereas the compounds of the present invention retain the excellent flame retardant performance.

TABLE 3

(flame tests on 1 mm compression molded plaques according to DIN 4102-B2, edge ignition, 20 mm flame, PDR100412): Low values for weight loss and burn length reflect increased flame retardancy.

| Example | Additives | Weight loss [%] | Burn length [mm] | Pass/Fail |
|---|---|---|---|---|
| Inventive 3 | 0.25% | 13.7 | 42 | Pass |
| Inventive 4 | 0.50% | 14.0 | 43 | Pass |

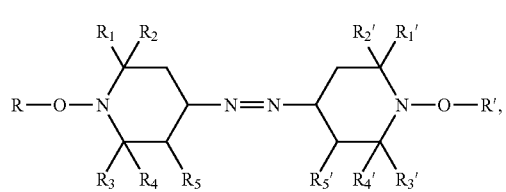

The invention claimed is:

1. A compound of the formula $$\text{R—O—N} \begin{smallmatrix} R_1 & R_2 \\ & \\ R_3 & R_4 & R_5 \end{smallmatrix} \text{—N=N—} \begin{smallmatrix} R_2' & R_1' \\ & \\ R_5' & R_4' & R_3' \end{smallmatrix} \text{N—O—R'}, \quad (I)$$

Wherein

R represents $C_1$-$C_{20}$alkyl, hydroxy-$C_2$-$C_8$alkyl, $C_1$-$C_{20}$alkanoyl, $C_7$-$C_{13}$aroyl, $C_2$-$C_{20}$alkenyl, $C_1$-$C_{20}$alkyl or $C_2$-$C_{20}$alkenyl interrupted by at least one heteroatom selected from the group consisting of O, S and N, $C_6$-$C_{20}$aryl, $C_1$-$C_{12}$alkyl-$C_6$-$C_{20}$aryl, $C_6$-$C_{20}$aryl, $C_6$-$C_{20}$aryl-$C_1$-$C_4$alkyl, mono- or bicyclic $C_5$-$C_{20}$cycloalkyl, mono- or bicyclic $C_1$-$C_{12}$alkyl-$C_5$-$C_{20}$cycloalkyl, or mono- or bicyclic $C_5$-$C_{20}$cycloalkyl-$C_1$-$C_4$alkyl;

$R_1$, $R_2$, $R_3$ and $R_4$ independently of one another represent hydrogen or $C_1$-$C_3$alkyl;

$R_5$ represents hydrogen or methyl; and

R', $R_1'$, $R_2'$, $R_3'$, $R_4'$ and $R_5'$ are as defined as R, $R_1$, $R_2$, $R_3$, $R_4$ and $R_5$.

2. A compound (I) according to claim 1, wherein represents $C_1$-$C_8$alkyl, hydroxy-$C_2$-$C_8$alkyl, $C_1$-$C_8$alkanoyl, phenyl, ($C_1$-$C_4$alkyl)$_{1-3}$phenyl, phenyl-$C_1$-$C_4$alkyl, $C_5$-$C_6$cycloalkyl, ($C_1$-$C_4$alkyl)$_{1-3}$$C_5$-$C_6$cycloalkyl, or ($C_1$-$C_4$alkyl)$_{1-3}$$C_5$-$C_6$cycloalkyl-$C_1$-$C_4$alkyl;

$R_1$, $R_2$, $R_3$ and $R_4$ represent methyl; or

One of $R_1$ and $R_2$ and one of $R_3$ and $R_4$ represents methyl and the other one represents ethyl;

$R_5$ represents hydrogen; and

R', $R_1'$, $R_2'$, $R_3'$, $R_4'$ and $R_5'$ are as defined as R, $R_1$, $R_2$, $R_3$, $R_4$ and $R_5$.

3. A compound (I) according to claim 1, wherein

R represents $C_1$-$C_8$alkyl, hydroxy-$C_2$-$C_8$alkyl, $C_1$-$C_8$alkanoyl, phenyl or $C_5$-$C_6$cycloalkyl;

$R_1$, $R_2$, $R_3$ and $R_4$ represent methyl; and $R_5$ represents hydrogen; and R', $R_1'$, $R_2'$, $R_3'$, $R_4'$ and $R_5'$ are as defined as R, $R_1$, $R_2$, $R_3$, $R_4$ and $R_5$.

4. A compound (I) according to claim 1, wherein
R represents $C_1$-$C_4$alkyl, hydroxy-$C_2$-$C_4$alkyl, $C_1$-$C_4$alkanoyl, phenyl or $C_5$-$C_6$cycloalkyl;
$R_1$, $R_2$, $R_3$ and $R_4$ represent methyl; and
$R_5$ represents hydrogen; and
R', $R_1$', $R_2$', $R_3$', $R_4$' and $R_5$' are as defined as R, $R_1$, $R_2$, $R_3$, $R_4$ and $R_5$.

5. A compound (I) according to claim 1 selected from the group consisting of

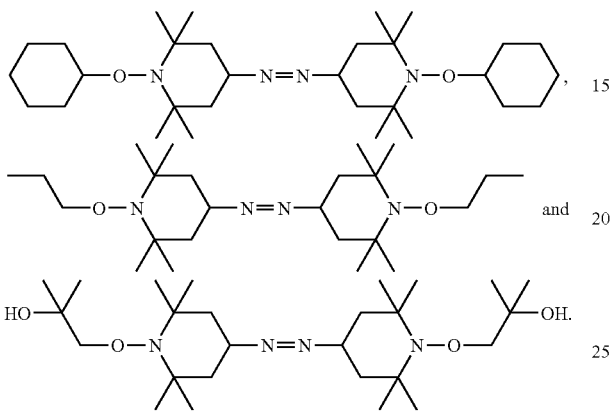

6. A composition, which comprises
c) A polymer substrate and
d) A compound of the formula

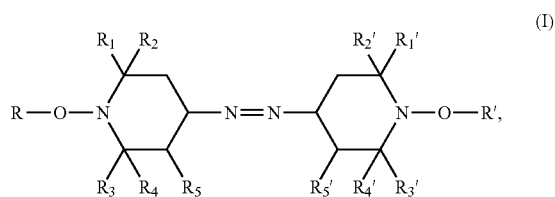

Wherein
R represents $C_1$-$C_{20}$alkyl, hydroxy-$C_2$-$C_8$alkyl, $C_1$-$C_{20}$alkanoyl, $C_2$-$C_{20}$alkenyl, $C_1$-$C_{20}$alkyl or $C_2$-$C_{20}$alkenyl interrupted by at least one heteroatom selected from the group consisting of O, S and N, $C_2$-$C_{20}$alkinyl, $C_5$-$C_{20}$aryl, $C_1$-$C_{12}$alkyl-$C_5$-$C_{20}$aryl, $C_5$-$C_{20}$aryl-$C_1$-$C_4$alkyl, mono- or bicyclic $C_5$-$C_{20}$cycloalkyl, mono- or bicyclic $C_1$-$C_{12}$alkyl-$C_5$-$C_{20}$cycloalkyl, or mono- or bicyclic $C_5$-$C_{20}$cycloalkyl-$C_1$-$C_4$alkyl;
$R_1$, $R_2$, $R_3$ and $R_4$ independently of one another represent hydrogen or $C_1$-$C_3$alkyl;
$R_5$ represents hydrogen or methyl; and
R', $R_1$', $R_2$', $R_3$', $R_4$' and $R_5$' are as defined as R, $R_1$, $R_2$, $R_3$, $R_4$ and $R_5$.

7. A composition according to claim 6 which additionally comprises further additives selected from the group consisting of polymer stabilizers and additional flame-retardants.

8. A process for imparting flame retardancy to a polymer substrate, which process comprises adding to said polymer substrate the compound (I) according to claim 1.

* * * * *